(12) United States Patent
Surti et al.

(10) Patent No.: US 9,375,219 B2
(45) Date of Patent: Jun. 28, 2016

(54) MEDICAL DEVICES WITH DETACHABLE PIVOTABLE JAWS

(71) Applicant: Cook Medical Technologies LLC, Bloomingon, IN (US)

(72) Inventors: Vihar C. Surti, Winston-Salem, NC (US); Michelle D. Martinez, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 232 days.

(21) Appl. No.: 14/285,009

(22) Filed: May 22, 2014

(65) Prior Publication Data

US 2014/0257343 A1     Sep. 11, 2014

Related U.S. Application Data

(62) Division of application No. 12/971,873, filed on Dec. 17, 2010, now Pat. No. 8,771,293.

(60) Provisional application No. 61/289,297, filed on Dec. 22, 2009.

(51) Int. Cl.
*A61B 17/10* (2006.01)
*A61B 17/128* (2006.01)
(Continued)

(52) U.S. Cl.
CPC ............. *A61B 17/1285* (2013.01); *A61B 17/08* (2013.01); *A61B 17/10* (2013.01); *A61B 17/122* (2013.01); *A61B 17/29* (2013.01); *A61B 2017/00473* (2013.01); *A61B 2017/12004* (2013.01); *A61B 2017/2902* (2013.01);
(Continued)

(58) Field of Classification Search
CPC ...... A61B 17/08; A61B 17/10; A61B 17/122; A61B 17/128; A61B 17/1285; A61B 2017/00473; A61B 2017/2902; A61B 2017/2931; A61B 2017/2943; A61B 2017/294; A61B 2017/2944; A61B 1/00101; A61B 18/1447
See application file for complete search history.

(56) References Cited

U.S. PATENT DOCUMENTS 720,385 A    2/1903   Storle
2,384,697 A  9/1945   Riccardi
(Continued)

FOREIGN PATENT DOCUMENTS

DE    4404766 A1    8/1995
DE    19534320      2/1997
(Continued)

OTHER PUBLICATIONS

Product brochure entitled "Hemostatic Grasper", 2014 Olympus America, Inc., Jul. 1, 2014, pp. 1-3 (https://medical.olympusamerica.com/products/coagrasper).

(Continued)

*Primary Examiner* — Julian W Woo
*Assistant Examiner* — Shaun L David
(74) *Attorney, Agent, or Firm* — Brinks Gilson & Lione

(57) ABSTRACT

Medical systems, devices and methods are provided for engaging tissue, e.g. for clipping tissue, closing a perforation or performing hemostasis. Generally, the medical system including a housing, first and second jaws rotatable relative to the housing, a driver, and an elongate drive wire. The elongate drive wire may be disconnected from the driver, first and second jaws, and the housing, which are left in vivo engaged with the tissue.

20 Claims, 9 Drawing Sheets

(51) Int. Cl.
*A61B 17/08* (2006.01)
*A61B 17/122* (2006.01)
*A61B 17/29* (2006.01)
*A61B 17/00* (2006.01)
*A61B 17/12* (2006.01)

(52) U.S. Cl.
CPC . *A61B2017/2931* (2013.01); *A61B 2017/2936* (2013.01); *A61B 2017/2943* (2013.01); *A61B 2017/2944* (2013.01)

(56) References Cited

U.S. PATENT DOCUMENTS

| | | |
|---|---|---|
| 2,598,901 A | 6/1952 | Garland |
| 2,614,445 A | 10/1952 | Riordan |
| 3,363,628 A | 1/1968 | Wood |
| 3,463,156 A | 8/1969 | McDermott |
| 3,481,641 A | 12/1969 | Berger et al. |
| 3,867,944 A | 2/1975 | Samuels |
| 3,924,303 A | 12/1975 | Elliott |
| 3,932,918 A | 1/1976 | Paskert |
| 3,958,576 A | 5/1976 | Komiya |
| 4,453,756 A | 6/1984 | Haag |
| 4,467,802 A | 8/1984 | Maslanka |
| 4,512,345 A | 4/1985 | Green |
| 4,519,392 A | 5/1985 | Lingua |
| 4,569,131 A | 2/1986 | Falk et al. |
| 4,733,664 A | 3/1988 | Kirsch et al. |
| 4,763,668 A | 8/1988 | Macek et al. |
| 4,765,335 A | 8/1988 | Schmidt et al. |
| 4,805,618 A | 2/1989 | Ueda et al. |
| 4,822,348 A | 4/1989 | Casey |
| 4,950,273 A | 8/1990 | Briggs |
| 4,990,152 A | 2/1991 | Yoon |
| 5,029,355 A | 7/1991 | Thai |
| 5,049,153 A | 9/1991 | Nakao et al. |
| 5,100,418 A | 3/1992 | Yoon et al. |
| 5,100,430 A | 3/1992 | Avellanet et al. |
| 5,133,727 A | 7/1992 | Bales et al. |
| 5,141,519 A | 8/1992 | Smith et al. |
| 5,147,357 A | 9/1992 | Rose et al. |
| 5,152,778 A | 10/1992 | Bales, Jr. et al. |
| 5,156,609 A | 10/1992 | Nakao et al. |
| 5,174,276 A | 12/1992 | Crockard |
| 5,192,298 A | 3/1993 | Smith et al. |
| 5,201,743 A | 4/1993 | Haber et al. |
| 5,209,747 A | 5/1993 | Knoepfler |
| 5,211,655 A | 5/1993 | Hasson |
| 5,222,961 A | 6/1993 | Nakao et al. |
| 5,242,456 A | 9/1993 | Nash et al. |
| 5,275,608 A | 1/1994 | Forman et al. |
| 5,275,613 A | 1/1994 | Haber et al. |
| 5,275,615 A | 1/1994 | Rose |
| 5,282,806 A | 2/1994 | Haber et al. |
| 5,304,183 A | 4/1994 | Gourlay et al. |
| 5,306,283 A | 4/1994 | Conners |
| 5,318,589 A | 6/1994 | Lichtman |
| 5,368,606 A | 11/1994 | Marlow et al. |
| 5,407,243 A | 4/1995 | Riemann |
| 5,423,857 A | 6/1995 | Rosenman et al. |
| 5,471,992 A * | 12/1995 | Banik ............... A61B 10/0266 600/564 |
| 5,474,569 A | 12/1995 | Zinreich et al. |
| 5,499,998 A | 3/1996 | Meade |
| 5,501,693 A | 3/1996 | Gravener |
| 5,509,923 A | 4/1996 | Middleman et al. |
| 5,520,701 A | 5/1996 | Lerch |
| 5,569,274 A | 10/1996 | Rapacki et al. |
| 5,571,137 A | 11/1996 | Marlow et al. |
| 5,618,303 A | 4/1997 | Marlow et al. |
| 5,620,452 A | 4/1997 | Yoon |
| 5,626,607 A | 5/1997 | Malecki et al. |
| 5,632,764 A | 5/1997 | Beideman et al. |
| 5,634,932 A | 6/1997 | Schmidt |
| 5,702,407 A | 12/1997 | Kaji |
| 5,766,184 A | 6/1998 | Matsuno et al. |
| 5,766,189 A | 6/1998 | Matsuno |
| 5,782,748 A * | 7/1998 | Palmer ............... A61B 10/06 600/104 |
| 5,792,165 A | 8/1998 | Kilieman et al. |
| 5,797,923 A | 8/1998 | Aiyar et al. |
| 5,797,939 A | 8/1998 | Yoon |
| 5,846,255 A | 12/1998 | Casey |
| 5,893,863 A | 4/1999 | Yoon |
| 5,893,875 A * | 4/1999 | O'Connor ............ A61B 17/29 606/167 |
| 5,893,878 A | 4/1999 | Pierce |
| 5,902,310 A | 5/1999 | Foerster et al. |
| 5,964,779 A | 10/1999 | Mayenberger et al. |
| 6,010,523 A * | 1/2000 | Sabin ............... A61B 10/06 600/562 |
| 6,059,719 A | 5/2000 | Yamamoto et al. |
| 6,106,041 A | 8/2000 | Eckhardt |
| 6,139,563 A | 10/2000 | Cosgrove, III et al. |
| 6,358,197 B1 | 3/2002 | Silverman et al. |
| 6,386,496 B1 | 5/2002 | Lai et al. |
| 6,464,710 B1 | 10/2002 | Foster |
| 6,613,059 B2 | 9/2003 | Schaller et al. |
| 6,814,742 B2 | 11/2004 | Kimura et al. |
| 6,923,818 B2 | 8/2005 | Muramatsu et al. |
| 6,991,634 B2 | 1/2006 | Sugiyama et al. |
| 7,011,667 B2 | 3/2006 | Kobayashi et al. |
| 7,041,118 B2 | 5/2006 | Muramatsu et al. |
| 7,081,121 B2 | 7/2006 | Muramatsu et al. |
| 7,175,649 B2 | 2/2007 | Machold et al. |
| 7,207,997 B2 | 4/2007 | Shipp et al. |
| 7,223,271 B2 | 5/2007 | Muramatsu et al. |
| 7,223,272 B2 | 5/2007 | Francese et al. |
| 7,326,221 B2 | 2/2008 | Sakamoto |
| 7,452,327 B2 * | 11/2008 | Durgin ............... A61B 17/122 600/104 |
| 7,488,334 B2 | 2/2009 | Jugenheimer et al. |
| 7,494,461 B2 | 2/2009 | Wells et al. |
| 7,601,159 B2 | 10/2009 | Ewers et al. |
| 7,722,628 B2 | 5/2010 | Stokes et al. |
| 7,727,247 B2 | 6/2010 | Kimura et al. |
| 7,736,372 B2 | 6/2010 | Reydel et al. |
| 7,736,374 B2 | 6/2010 | Vaughan et al. |
| 7,740,639 B2 | 6/2010 | Hummel et al. |
| 7,744,613 B2 | 6/2010 | Ewers et al. |
| 7,766,810 B2 | 8/2010 | Ohdaira |
| 7,776,057 B2 | 8/2010 | Laufer et al. |
| 7,815,652 B2 | 10/2010 | Messerly et al. |
| 7,896,895 B2 | 3/2011 | Boudreaux et al. |
| 8,062,311 B2 | 11/2011 | Litscher et al. |
| 8,083,668 B2 | 12/2011 | Durgin et al. |
| 8,088,061 B2 | 1/2012 | Wells et al. |
| 8,172,859 B2 | 5/2012 | Matsuno et al. |
| 8,317,820 B2 | 11/2012 | Surti |
| 8,348,964 B2 | 1/2013 | Kimura et al. |
| 8,545,519 B2 | 10/2013 | Aguirre et al. |
| 8,709,027 B2 | 4/2014 | Adams et al. |
| 8,771,293 B2 | 7/2014 | Surti et al. |
| 8,858,588 B2 | 10/2014 | Sigmon, Jr. et al. |
| 2002/0045909 A1 | 4/2002 | Kimura et al. |
| 2002/0151916 A1 | 10/2002 | Muramatsu et al. |
| 2002/0173805 A1 | 11/2002 | Matsuno et al. |
| 2002/0177861 A1 | 11/2002 | Sugiyama et al. |
| 2003/0069592 A1 | 4/2003 | Adams et al. |
| 2003/0097146 A1 | 5/2003 | Montalvo et al. |
| 2004/0044363 A1 | 3/2004 | Fowler |
| 2005/0059985 A1 | 3/2005 | Kimura |
| 2005/0101991 A1 | 5/2005 | Ahlberg et al. |
| 2005/0234296 A1 | 10/2005 | Saadat et al. |
| 2005/0251183 A1 | 11/2005 | Buckman et al. |
| 2005/0272977 A1 | 12/2005 | Saadat et al. |
| 2006/0084886 A1 | 4/2006 | Reydel |
| 2006/0155308 A1* | 7/2006 | Griego ............... A61B 17/068 606/142 |
| 2006/0258905 A1* | 11/2006 | Kaji ............... A61B 1/00133 600/106 |
| 2006/0259045 A1 | 11/2006 | Damarati |
| 2007/0073185 A1 | 3/2007 | Nakao |
| 2007/0135678 A1 | 6/2007 | Suzuki |

(56) References Cited

U.S. PATENT DOCUMENTS

| | | |
|---|---|---|
| 2007/0239162 A1 | 10/2007 | Bhatnagar et al. |
| 2007/0250113 A1 | 10/2007 | Hegeman et al. |
| 2007/0282355 A1* | 12/2007 | Brown .............. A61B 17/122 606/151 |
| 2007/0287993 A1 | 12/2007 | Hinman et al. |
| 2008/0004656 A1* | 1/2008 | Livneh ............... A61B 17/29 606/205 |
| 2008/0147113 A1 | 6/2008 | Nobis et al. |
| 2008/0171907 A1 | 7/2008 | Long et al. |
| 2008/0228199 A1 | 9/2008 | Cropper et al. |
| 2008/0228202 A1 | 9/2008 | Cropper et al. |
| 2008/0234703 A1 | 9/2008 | Cropper et al. |
| 2008/0234705 A1 | 9/2008 | Cropper et al. |
| 2008/0255427 A1 | 10/2008 | Satake et al. |
| 2008/0262539 A1 | 10/2008 | Ewers et al. |
| 2008/0269557 A1 | 10/2008 | Marescaux et al. |
| 2008/0269566 A1 | 10/2008 | Measamer |
| 2008/0275441 A1 | 11/2008 | Aue |
| 2008/0287963 A1 | 11/2008 | Rogers et al. |
| 2008/0294178 A1 | 11/2008 | Kortenbach et al. |
| 2008/0300461 A1 | 12/2008 | Shaw et al. |
| 2008/0300624 A1 | 12/2008 | Schwemberger et al. |
| 2009/0005638 A1 | 1/2009 | Zwolinski |
| 2009/0018602 A1 | 1/2009 | Mitelberg et al. |
| 2009/0043316 A1* | 2/2009 | Durgin ............... A61B 17/122 606/142 |
| 2009/0062792 A1 | 3/2009 | Vakharia et al. |
| 2009/0138006 A1 | 5/2009 | Bales et al. |
| 2009/0138028 A1 | 5/2009 | Wells et al. |
| 2009/0143794 A1 | 6/2009 | Conlon et al. |
| 2009/0163934 A1 | 6/2009 | Raschdorf, Jr. et al. |
| 2009/0192344 A1 | 7/2009 | Bakos et al. |
| 2009/0221915 A1 | 9/2009 | Voegele et al. |
| 2009/0299385 A1 | 12/2009 | Stefanchik et al. |
| 2009/0306683 A1 | 12/2009 | Zwolinski et al. |
| 2009/0306686 A1 | 12/2009 | Ohdaira |
| 2009/0326518 A1 | 12/2009 | Rabin |
| 2009/0326578 A1 | 12/2009 | Ewers et al. |
| 2010/0010512 A1* | 1/2010 | Taylor ................. A61B 17/04 606/144 |
| 2010/0042115 A1 | 2/2010 | Saadar et al. |
| 2010/0057078 A1 | 3/2010 | Arts et al. |
| 2010/0057085 A1 | 3/2010 | Holcomb et al. |
| 2010/0130817 A1 | 5/2010 | Conlon |
| 2010/0168787 A1 | 7/2010 | Surti |
| 2010/0179540 A1 | 7/2010 | Marczyk et al. |
| 2010/0198149 A1 | 8/2010 | Fox |
| 2010/0198248 A1 | 8/2010 | Vakharia |
| 2010/0211086 A1 | 8/2010 | Ewers et al. |
| 2010/0217151 A1 | 8/2010 | Gostout et al. |
| 2010/0217292 A1 | 8/2010 | Kimura et al. |
| 2010/0217293 A1 | 8/2010 | Kimura et al. |
| 2010/0217294 A1 | 8/2010 | Kumura et al. |
| 2010/0249498 A1 | 9/2010 | Wingardner et al. |
| 2010/0249700 A1 | 9/2010 | Spivey |
| 2010/0249808 A1 | 9/2010 | Harada et al. |
| 2011/0152888 A1 | 6/2011 | Ho et al. |
| 2012/0016391 A1 | 1/2012 | Aguirre |
| 2012/0051200 A1 | 3/2012 | Kodama |
| 2012/0089158 A1 | 4/2012 | Martenez et al. |
| 2012/0089176 A1 | 4/2012 | Sigmon, Jr. et al. |
| 2012/0109160 A1 | 5/2012 | Martenez et al. |
| 2012/0165863 A1 | 6/2012 | McLawhorn |
| 2012/0232338 A1* | 9/2012 | Livneh ............. A61B 1/00101 600/104 |

FOREIGN PATENT DOCUMENTS

| | | |
|---|---|---|
| DE | 19750878 A1 | 5/1999 |
| DE | 19906360 A1 | 8/2000 |
| DE | 102006003548 | 8/2007 |
| EP | 0246087 A3 | 11/1987 |
| EP | 0541930 A1 | 5/1993 |
| EP | 0738501 A1 | 10/1996 |
| FR | 790997 | 11/1935 |
| JP | 57-156752 | 9/1982 |
| JP | 60-103946 | 6/1985 |
| JP | 63-6016 | 2/1988 |
| JP | 63-267345 | 11/1988 |
| JP | 63-288147 | 11/1988 |
| JP | 2-6011 | 1/1990 |
| JP | 2007950 | 1/1990 |
| JP | 4-26091 | 3/1992 |
| JP | 4102450 | 4/1992 |
| JP | 5-212043 | 8/1993 |
| JP | 5208020 | 8/1993 |
| JP | 5212042 | 8/1993 |
| JP | 6237939 | 8/1994 |
| JP | 6254101 | 9/1994 |
| JP | 8019548 | 1/1996 |
| JP | 8126648 | 5/1996 |
| JP | 8280701 | 10/1996 |
| JP | 8308847 | 11/1996 |
| JP | 9038093 | 2/1997 |
| JP | 9289989 | 11/1997 |
| JP | 2000-33090 | 2/2000 |
| JP | 2000-335631 | 12/2000 |
| JP | 2001-520069 | 10/2001 |
| JP | 2002-224124 | 8/2002 |
| JP | 2002-301082 | 10/2002 |
| JP | 2002-360585 | 12/2002 |
| WO | WO 9614020 | 5/1996 |
| WO | WO 99/20183 | 4/1999 |
| WO | WO 2004/017839 | 4/2004 |
| WO | WO 2008/005433 | 1/2008 |
| WO | WO 2010/078163 | 7/2010 |
| WO | WO 2011/087723 | 7/2011 |
| WO | WO 2012/051188 | 4/2012 |
| WO | WO 2012/051191 | 4/2012 |
| WO | WO 2012/051200 | 4/2012 |
| WO | WO 2012/083041 | 6/2012 |
| WO | WO 2012/051200 | 11/2012 |

OTHER PUBLICATIONS

Product brochure entitled "Titanium Hemostatic Clip", Jorgensen Laboratories, Inc., Loveland, Colorado 80538.
International Search Report and Opinion for PCT/US2011/055800 (Sep. 12, 2012).
International Search Report and Opinion for PCT/US2012/046666 (Oct. 8, 2012).
Office Action dated Jan. 18, 2012 for U.S. Appl. No. 12/645,004 in related application.
Office Action dated May 29, 2012 for U.S. Appl. No. 12/645,004 in related application.
Office Action dated Dec. 20, 2012 for U.S. Appl. No. 13/186,427 in related application.
Office Action dated May 6, 2013 for U.S. Appl. No. 12/971,873 in related application.
Office Action dated Nov. 6, 2013 for U.S. Appl. No. 12/971,873 in related application.
Office Action dated Mar. 10, 2014 for U.S. Appl. No. 13/270,851 in related application.
Office Action dated Mar. 17, 2014 for U.S. Appl. No. 13/270,834 in related application.
Office Action dated Feb. 26, 2014 for U.S. Appl. No. 13/327,127 in related application.
International Search Report/Written Opinion for PCT/US2009/069270 (May 17, 2010).
International Search Report/Written Opinion for PCT/US2010/061077 (Apr. 1, 2011).
OLYMPUS Endo Therapy brochure on the QuickClip2 Long.
CooperSurgical brochure on the Marlow Nu-Tip Laparoscopic Instruments.
Medwork brochure,Endo Therapy for the Clipmaster 3.
Boston Scientific Catalog on the Resolution Clip Device.
Medicon Instrument Catalog, pp. 440, 441, 443, 451, 585, 686 (1986).
V. Mueller, The Surgical Armamentarium, pp. F176-F177 (1988).

(56) References Cited

OTHER PUBLICATIONS

Annex to Form PCT/ISA/206—Communication Relating to the Results of Partial International Search for PCT/US2011/055800 (Jun. 28, 2012).
International Search Report and Opinion for PCT/US2011/055780 (Jun. 14, 2012).
International Search Report and Opinion for PCT/US2011/055786 (Jun. 19, 2012).
International Search Report and Opinion for PCT/US2011/065200 (Jun. 13, 2012).
Office Action dated Dec. 24, 2013 U.S. Appl. No. 13/270,784 in related application.

* cited by examiner

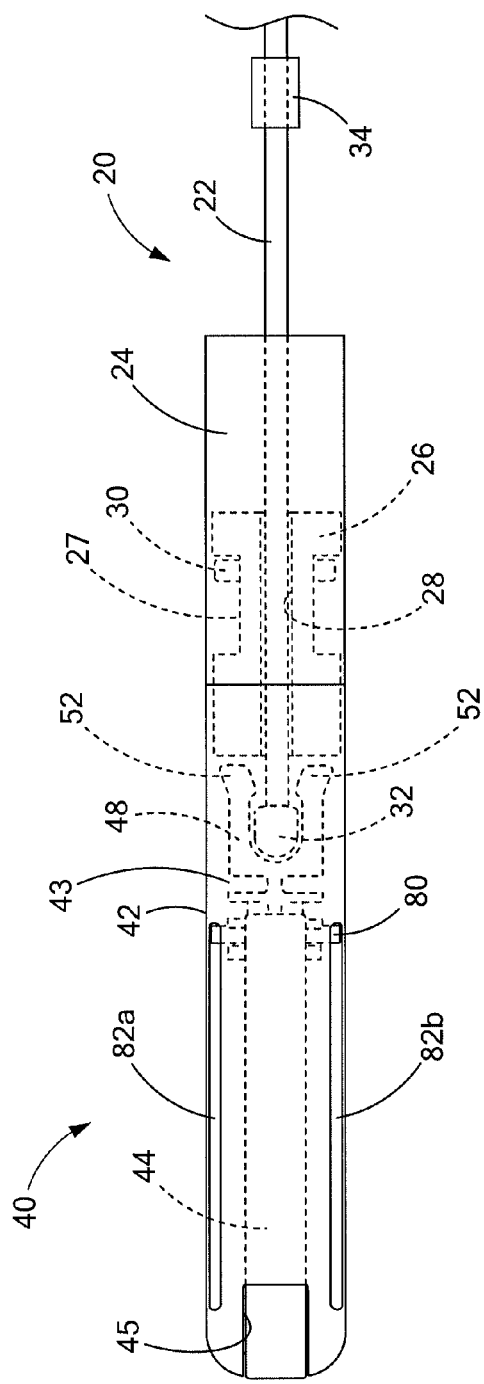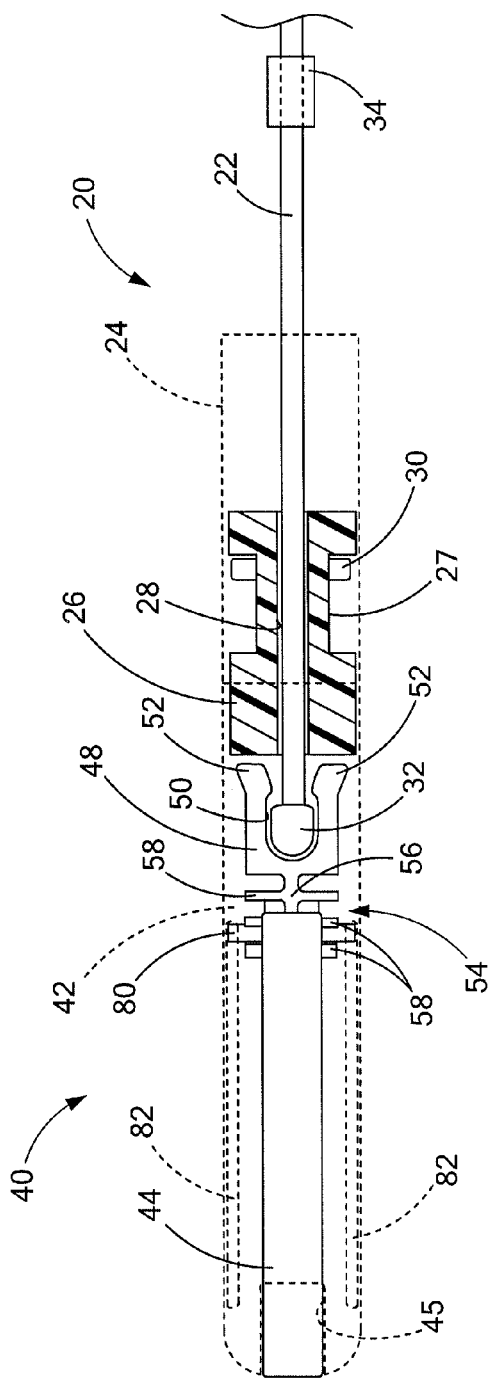

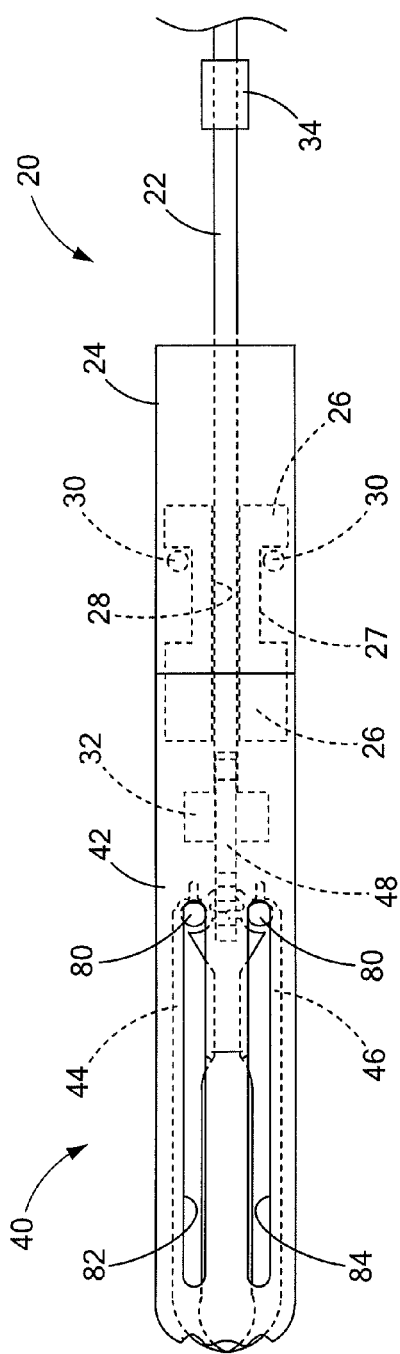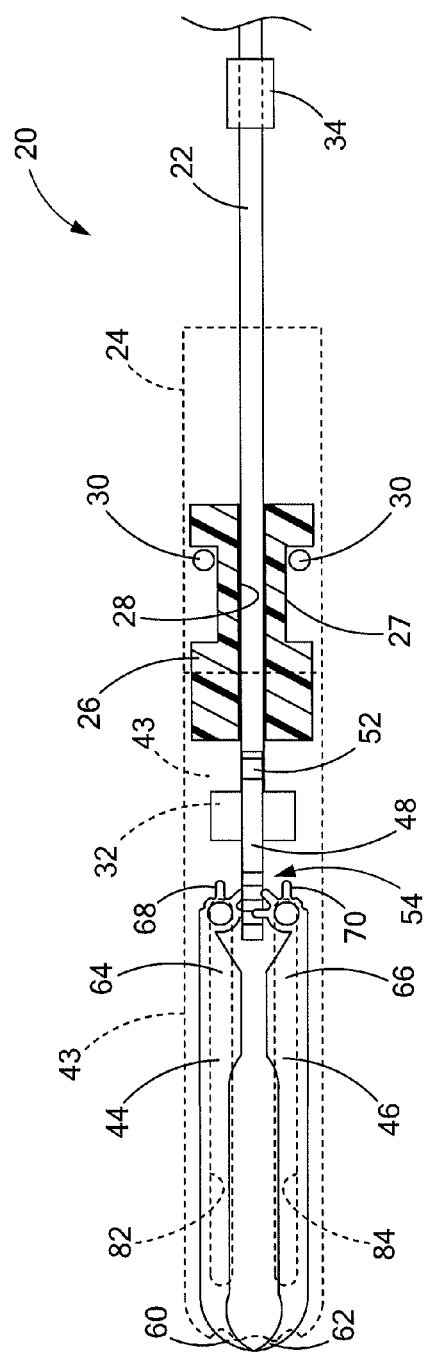
FIG. 3
FIG. 4

MEDICAL DEVICES WITH DETACHABLE PIVOTABLE JAWS

CROSS-REFERENCE TO RELATED APPLICATIONS

This application is a Divisional of U.S. patent application Ser. No. 12/971,873 filed on Dec. 17, 2010, and also claims the benefit of U.S. Provisional Patent Application Ser. No. 61/289,297 filed on Dec. 22, 2009, entitled "MEDICAL DEVICES WITH DETACHABLE PIVOTABLE JAWS", all of the foregoing applications are hereby incorporated herein by reference.

BACKGROUND

Conventionally, a clip may be introduced into a body cavity through an endoscope to grasp living tissue of a body cavity for hemostasis, marking, and/or ligating. Such clips are often known as surgical clips, endoscopic clips, hemostasis clips and vascular clips. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding. Clips have also been attempted for use in closing perforations in the stomach Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices such as clips have been used in various parts of the body, including gastrointestinal applications. One of the problems associated with conventional hemostatic devices and clips, however, is that many devices are not strong enough to cause permanent hemostasis. Further, clips have also been attempted for use in closing perforations in the stomach or gastrointestinal structures, but unfortunately traditional clips suffer from difficult placement and the capability to grasp a limited amount of tissue, potentially resulting in incomplete closure.

SUMMARY

The invention may include any of the following aspects in various combinations and may also include any other aspect described below in the written description or in the attached drawings.

In a first aspect, a medical device is provided for engaging tissue, the medical device including a housing, first and second jaws pivotally connected to the housing, and a driver. The housing defines an internal passageway and a longitudinal axis extending between proximal and distal ends of the housing. The housing defines first and second guide surfaces along the internal passageway. The first and second jaws are slidably and pivotally connected to the housing, and each has proximal and distal ends. The first jaw is slidably received within the internal passageway for longitudinal movement along the first guide surface between an extended position and a retracted position. The second jaw is slidably received within the internal passageway for longitudinal movement along the second guide surface between an extended position and a retracted position. The housing is structured to block rotation of the first and second jaws when in their retracted positions, and structured to permit rotation of the first and second jaws when in their extended positions. The driver is engaged with the proximal ends of the first and second jaws, whereby longitudinal movement of the driver moves the first and jaws longitudinally along the first and second guides between their retracted and extended positions. Longitudinal movement of the driver rotates the first and second jaws relative to the housing when the first and second jaws are in their extended positions.

According to more detailed aspects, the proximal ends of the first and second jaws are located adjacent the distal end of the housing when the first and second jaws are in their extended positions. The proximal ends of the first and second jaws are slidably and pivotally attached to the housing. The housing defines a shoulder within the internal passageway, and the driver includes a locking tab positioned to engage the shoulder to limit longitudinal movement of the driver and the first and second jaws. The shoulder moves the locking tab to a position out of engagement with the shoulder when a distally directed longitudinal force on the driver reaches a predetermined force to permit longitudinal movement of the driver and the first and second jaws in a distal direction. Preferably the housing defines a third guide surface that guides longitudinal movement of the driver within the housing. The third guide surface may define the shoulder.

According to still further detailed aspects, the device may also include an elongate drive wire. The elongate drive wire is selectively connected to the driver for longitudinal movement therewith, and the locking tab firmly engages the drive wire when the locking tab is positioned distal to the shoulder, and the locking tab does not firmly engage the drive wire when the locking tab is positioned proximal to the shoulder to permit the drive wire to be disconnected from the driver. The drive wire may have an enlarged distal head, and the driver includes a socket sized to selectively receive the enlarged distal head of the drive wire. The socket faces proximally and is preferably constructed of a resilient material that flexes to adjust the size of the socket. The proximal ends of the first and second jaws include geared teeth, and the driver includes corresponding teeth that mesh with the geared teeth of the jaws. Preferably the proximal ends of the first and second jaws are formed as pinions, and the driver is formed as a rack, wherein longitudinal movement of the driver and rack rotates the pinions and first and second jaws in their extended positions. The driver includes a central spine extending longitudinally and teeth extending laterally from the central spine. Preferably, the driver includes pairs of teeth extending in laterally opposite directions from the spine to form two sets of teeth, one of the two sets of teeth engaged with the pinion of the first jaw, the other of the two sets of teeth engaged with the pinion of the second jaw.

In a second aspect, a medical system is provided for engaging tissue, the medical system including a housing, first and second jaws pivotally connected to the housing, a driver and an elongate drive wire. The housing defines an internal passageway and a longitudinal axis extending between proximal and distal ends of the housing. The housing further defines a driver guide surface along the internal passageway, the driver guide surface including a proximal portion having a proximal width and a distal portion having a distal width. The proximal width is greater than a distal width. The driver is engaged with the proximal ends of the first and second jaws. Longitudinal movement of the driver rotates the first and second jaws relative to the housing. The driver further includes a moveable locking tab. The elongated drive wire selectively connects to the driver for longitudinal movement therewith. The locking tab firmly engages the drive wire when the tab is positioned along the distal portion of the driver guide surface, and the locking tab permits the drive wire to be disconnected from the driver when the locking tab is positioned along the proximal portion of the driver guide surface.

According to more detailed aspects, the elongated drive wire has a distal head and the driver includes a socket sized to receive the distal head. The locking tab is positioned at an entrance to the socket and moves to vary the size of the entrance. The driver includes two locking tabs on opposing sides of the socket, and the driver guide surface includes two surfaces on opposing sides of the housing corresponding to the two locking tabs. The medical system may further include a tubular connector defining a lumen sized to slidably receive a connection block. The connection block is structured to frictionally engage a proximal end of the housing and defines a bore slidably receiving the drive wire. A distal end of the drive wire defines a distal head having a size that is larger than the bore, wherein the distal head engages the connection block upon proximal retraction of the drive wire and slides proximally relative to the tubular connector to disengage the connection block from the housing.

According to still further aspects, the housing preferably defines a shoulder at the transition between the proximal portion and distal portion of the driver guide surface, and the locking tab is positioned to engage the shoulder to limit longitudinal movement of the driver. The shoulder deflects the tab to a position out of engagement with the shoulder when a distally directed longitudinal force on the driver reaches a predetermined force to permit longitudinal movement of the driver and the first and second jaws in a distal direction.

In a third aspect, a method is provided for clamping tissue. The method includes providing a medical device or system such as those described above and further herein. The drive wire is advanced distally to translate the first and second jaws distally relative to the housing. The drive wire is advanced distally to rotate the first and second jaws away from each other. The tissue is positioned between the first and second jaws, and the drive wire is retracted proximally to rotate the first and second jaws towards each other to clamp the tissue therebetween. The drive wire is retracted proximally to translate the first and second jaws proximally relative to the housing. The drive wire is detached from the driver to leave the first and second jaws clamped to the tissue and connected to the housing. According to further detailed aspects, the step of retracting the drive wire proximally to translate the first and second jaws proximally preferably includes restricting the distal movement of the driver to maintain the clamping of the tissue.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a top view of a medical system having a medical device for engaging tissue, constructed in accordance with the teachings of the present invention;

FIG. 2 is a top view similar to FIG. 1, but showing the outer structures in dotted lines and the interior sections in solid lines and partial cross section;

FIG. 3 is a side view of the medical system and device depicted in FIG. 1;

FIG. 4 is a side view similar to FIG. 3, but showing the outer structures in dotted lines and the interior structures in solid lines and partial cross section

DETAILED DESCRIPTION

Figure 5:
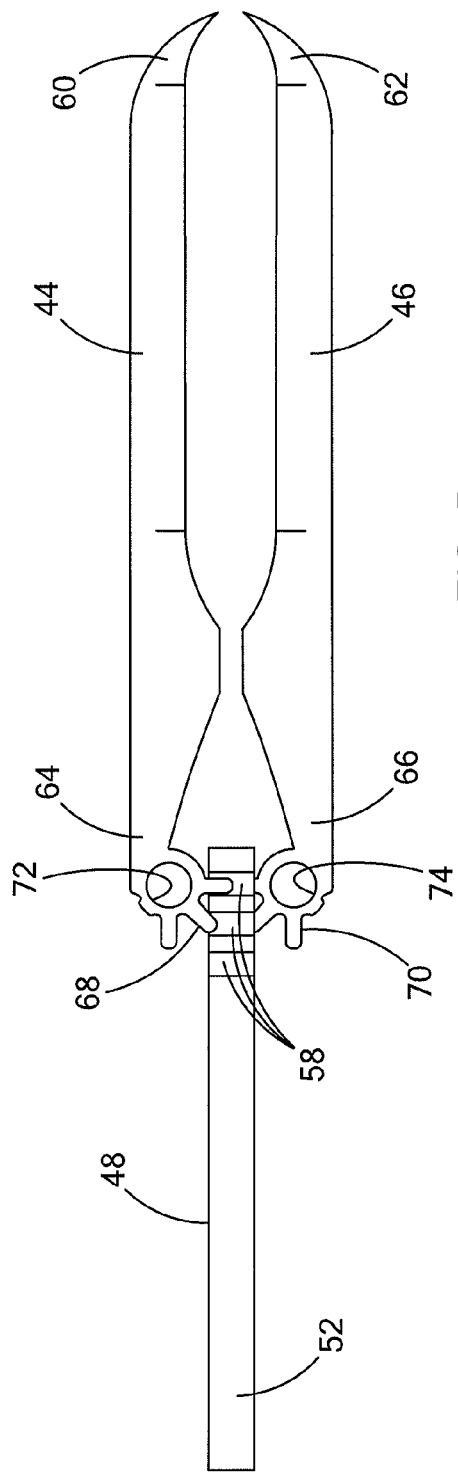
FIG. 5 is a side view of a medical device that is part of the medical system depicted in FIGS. 1-4.

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

An exemplary medical system 20 having a medical device 40 for engaging tissue T (FIG. 11) is shown in FIGS. 1 through 4. The medical system 20 and device 40 are generally sized and structured for operation through the working channel of an endoscope (not shown) or other scope, although the system 20 and device 40 may also be used in conjunction with other elongate devices such as catheters, fiber-optic visualization systems, needles and the like. Generally, the medical system 20 includes a drive wire 22 slidably housed by a sheath 23 and having a tubular connector 24 at the distal end for selective connection to, and operation of, the medical device 40. As will be described in further detail herein, the medical device 40 generally includes a housing 42 having a first jaw 44 and a second jaw 46 pivotally connected thereto for engaging the tissue T. Generally, the jaws 44, 46 have been shown as forming grasping forceps, although the jaws are intended to be used to clip tissue, e.g. to close an opening or for hemostasis. Accordingly, it will be recognized that the shape and structure of the jaws may take many forms and serve many purposes and functions, all in accordance with the teachings of the present invention.

In the medical system 20, the drive wire 22 slidably extends through the tubular connector 24. Although the term "wire" is used to refer to the drive wire 22, it will be recognized that any elongate control member capable of transmitting longitudinal force over a distance (such as is required in typical endoscopic, laparoscopic and similar procedures) may be used, and this includes plastic rods or tubes, single filament or multi-filament wires and the like. A connection block 26 is slidably fitted within the tubular connector 24 and defines a bore 28 therethrough which slidably receives the drive wire 22. The exterior of the connection block 26 includes a recessed portion 27, and a pin 30 is connected to the tubular connector 24 and fits within the recessed portion 27 to limit the longitudinal movement of the connection block 26.

A distal end of the drive wire 22 defines a distal head 32 that is sized larger than the drive wire 22, and likewise larger than the bore 28 and the connection block 26. As will be described later herein, the distal head 32 is used to slide the connection block 26 within the tubular connector 24 to disconnect the medical device 40 from the medical system 20. As also seen in FIGS. 1-4, the housing 42 of the medical device 40 is a tubular member defining an interior space 43. A proximal end of the housing 42 frictionally receives a distal end of the connection block 26 within the interior space 43 for selective connection therewith.

The internal passageway 43 of the housing 42 also receives the first and second jaws 44, 46 and a driver 48 which is used to interconnect the drive wire 22 to the jaws 44, 46. As best seen in FIGS. 1, 2 and 5, the driver 48 has a proximal portion which defines a socket 50 sized to receive enlarged distal head 32 of the drive wire 22. At the proximal entrance of the socket 50, two deflectable locking tabs 52 are formed which rotate relative to the remainder of the driver 48. The locking tabs 52 may be separately formed and pivotally attached to the driver 48, or may be integrally formed with the driver 48 and of a resilient material which flexes to permit rotation of the locking tabs 52 radially inwardly and radially outwardly. A distal portion of the driver 48 defines a rack 54 for engaging and operating the jaws 44, 46. In the depicted embodiment, the rack 54 includes a central spine 56 having teeth 58 projecting away from the central spine 56 and on opposite sides of the spine 56. One set of teeth 58 on one side of the spine 56 generally operate the first jaw 44 while the other set of teeth 58 on the other side of the spine 56 operate the second jaw 46. It will be recognized that the rack 54 may include a single set of teeth or other geared structures that interface with the jaws 44, 46.

As best seen in FIG. 5, the first and second jaws 44, 46 include distal ends 60, 62 that are structured to grasp and engage tissue, and preferably they have a talon shape as disclosed in 61/141,934 filed Dec. 31, 2008, the disclosure of which is incorporated herein by reference in its entirety. The proximal ends 64, 66 of the first and second jaws 44, 46 each include a pinion gear 68, 70 having a series of teeth. The teeth of the pinion 68, 70 mesh with the teeth of the rack 54 of the driver 48 such that longitudinal translation of the driver 48 induces rotation in the first and second jaws 44, 46 relative to one another. Generally, distal translation of the driver 48 causes the first and second jaws 44, 46 to rotate outwardly away from each other, while proximal retraction of the driver 48 causes the first and second jaws 44, 46 to rotate inwardly toward one another. Pins 80 are fitted through each the proximal ends of the jaws 44, 46, to pivotally connect the jaws to the housing 42. Other structures for forming a pivotal connection may be used, and preferably the pivotal connection is centrally arranged relative to the pinions 68, 70.

Figure 7:
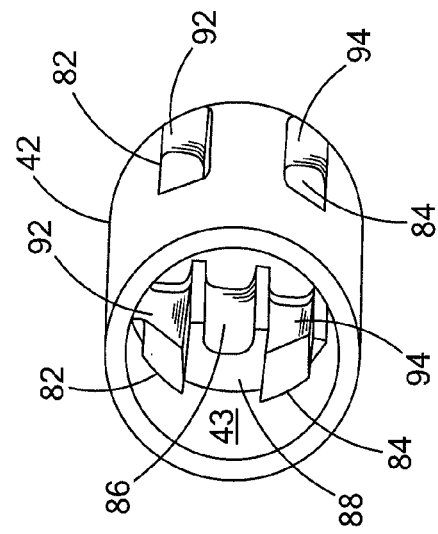
FIG. 7 is a perspective view of the housing depicted in FIG. 6.
Figure 6:
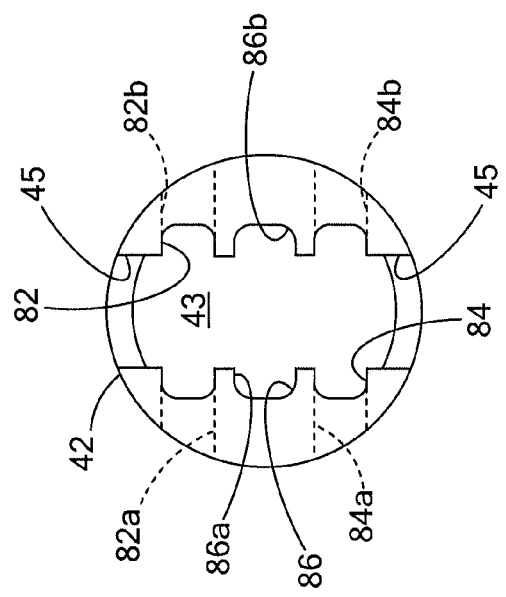
FIG. 6 is a front view of a housing forming a portion of the medical system and device depicted in FIGS. 1-5.

In addition to the jaws 44, 46 being pivotally attached to the housing 42, the first and second jaws 44, 46 are also slidably attached to the housing 42. As best seen in FIGS. 6 and 7 (and in conjunction with FIGS. 1-4) the housing 42 defines a first guide surface 82 for the first jaw 44, and a second guide surface 84 for the second jaw 46. As seen in FIG. 3, the first and second guide surfaces 82, 84 are formed by elongated slots 82a, 82b, 84a, 84b formed in opposing sides of the housing 42 which leaves a thickness of the housing 42 exposed to serve as the guide surface. The slots 82a, 82b are aligned to receive the connecting pin 80 of the first jaw 44, and likewise the slots 84a, 84b are aligned to receive the connecting pin 80 of the second jaw 46. The ends of the slots, for example distal ends 92, 94 shown in FIG. 7, serve to restrict the longitudinal movement of the jaws 44, 46 relative to the housing 42. The proximal ends 64, 66 of the jaws 44, 46 include apertures 72, 74 which receive the pins 80 (FIGS. 1, 2 and 3) that are used to slidably and pivotally connect the first and second jaws 44, 46 to the housing 42.

It can also be seen in FIGS. 6 and 7 that the housing 42 defines a third guide surface 86 which guides the longitudinal movement of the driver 48 within the housing 42. The guide surface 86 in the depicted embodiment includes a left guide surface 86a and a right guide surface 86b formed as C-shaped channels. As shown in FIG. 7, the third guide surface 86 transitions from a smaller proximal width to a larger distal width to define a shoulder 88 at the transition, which will be further described hereinbelow with reference to FIGS. 13 and 14. Various combinations of slots, guide surfaces, pins and other slidable engagement structures can be employed to connect the jaws to the housing.

As also shown in FIG. 6, the internal passageway 43 of the housing 42 extends through the distal end of the housing, and through which the first and second jaws 44, 46 can extend. Additionally, as shown in FIGS. 1 and 2, the housing 42 defines opposing slots 45 which are sized to permit the first and second jaws 44, 46 to pass therethrough when they rotate radially outwardly. Accordingly, it is also clear from FIGS. 1 and 2 that the housing 42 serves to block rotation of the first and second jaws 44, 46 when they are entirely or partially contained within the internal passageway 43 of the housing 42.

Figure 8:
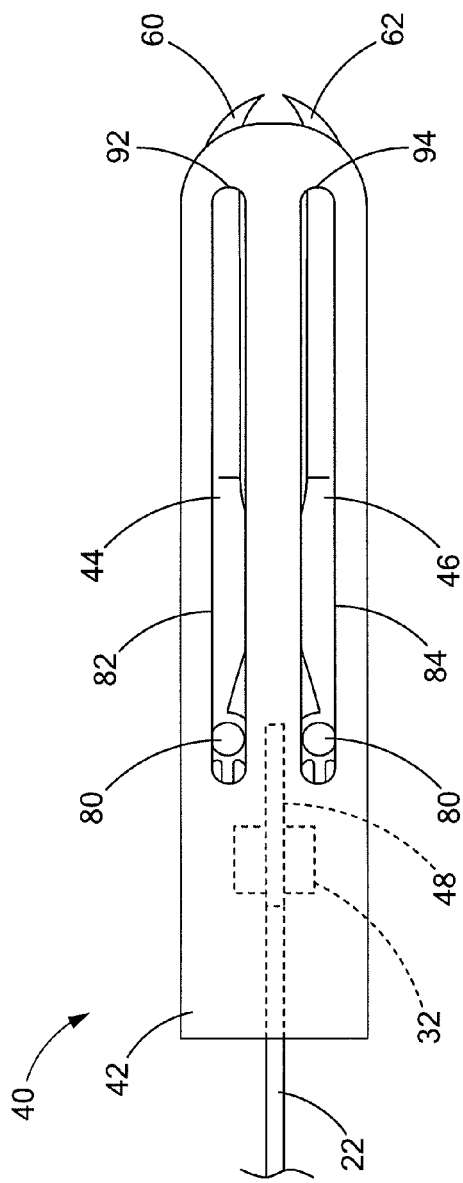
FIGS. 8-12 are side views showing operation of the medical system and device depicted in FIGS. 1-5.

Operation of the medical device 40 will now be described with reference to FIGS. 8-12. As shown in FIG. 8, the first and second jaws 44, 46 are shown in a retracted position where they are substantially contained within the housing 42. Depending on the application, the distal ends 60, 62 of the jaws 44, 46 may slightly project from the distal end of the housing 42 in their retracted positions, or they may be entirely positioned within the housing 42. When the drive wire 22 is translated distally (to the right on the page in FIG. 8) the distal head 32 engages the driver 48, and since the rack 54 of the driver 48 is meshed with the pinions 68, 70 at the proximal ends 64, 60 of the jaws 44, 46, the driver 48 and jaws 44, 46 slide distally through the housing 42 because the housing 42 blocks their rotation. As previously mentioned, this longitudinal movement is guided by the first and second guide surfaces 82, 84 which receive the pins 80 that slidably and pivotally connect the jaws 44, 46 to the housing 42.

Figure 9:
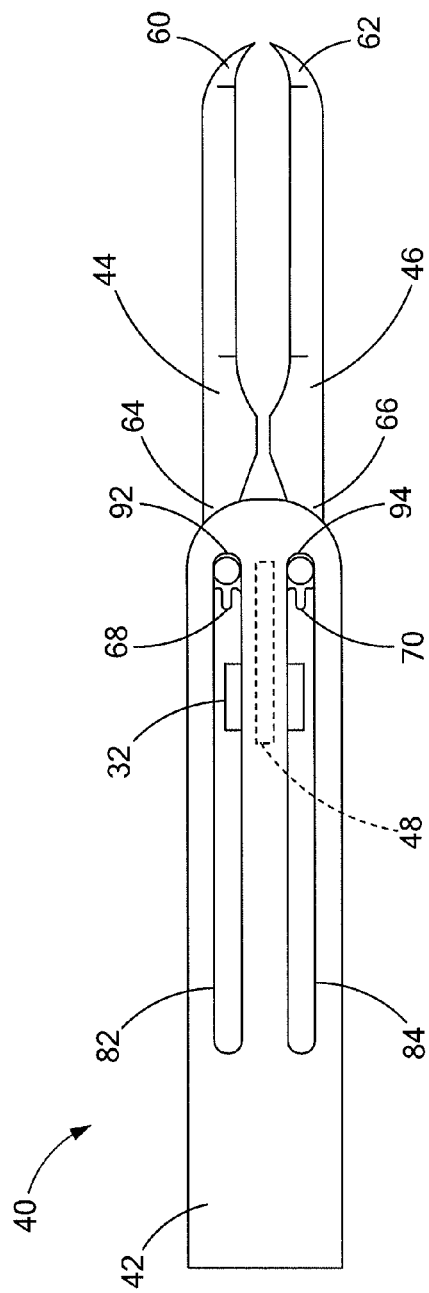
Figure 10:
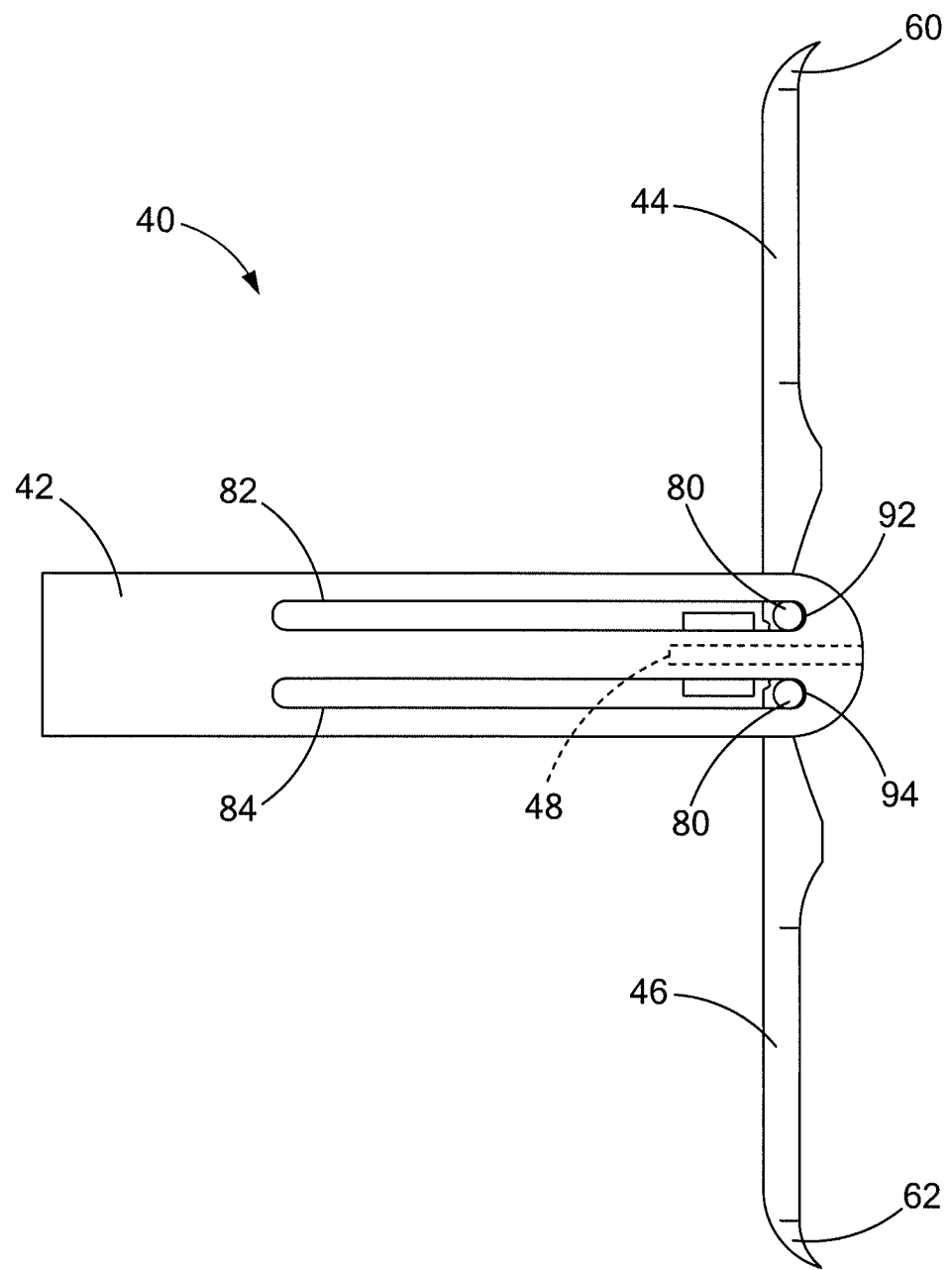

As shown in FIG. 9, the first and second jaws 44, 46 have an extended position where the jaws substantially project from a distal end of the housing 42, and their proximal ends 64, 66 are positioned adjacent the distal end of the housing 42. Accordingly, it will be seen that further distal advancement of drive wire 22, and hence the driver 48, causes the pinion 68 to rotate over the teeth 58 of the rack 54. As best seen in FIG. 10, the first and second jaws 44, 46 rotate radially outwardly from each other into a tissue receiving position. Notably, due to the presence of slots 45 at the distal end of the housing 42, the jaws 44, 46 are permitted to rotate a full 90°, thus forming at least a 180° between them. It will be recognized that through the sizing of the slots 45 and the construction of the rack 54 and pinions 68, 70, the first and second jaws 44, 46 may rotate even further away from each other.

Figure 11:
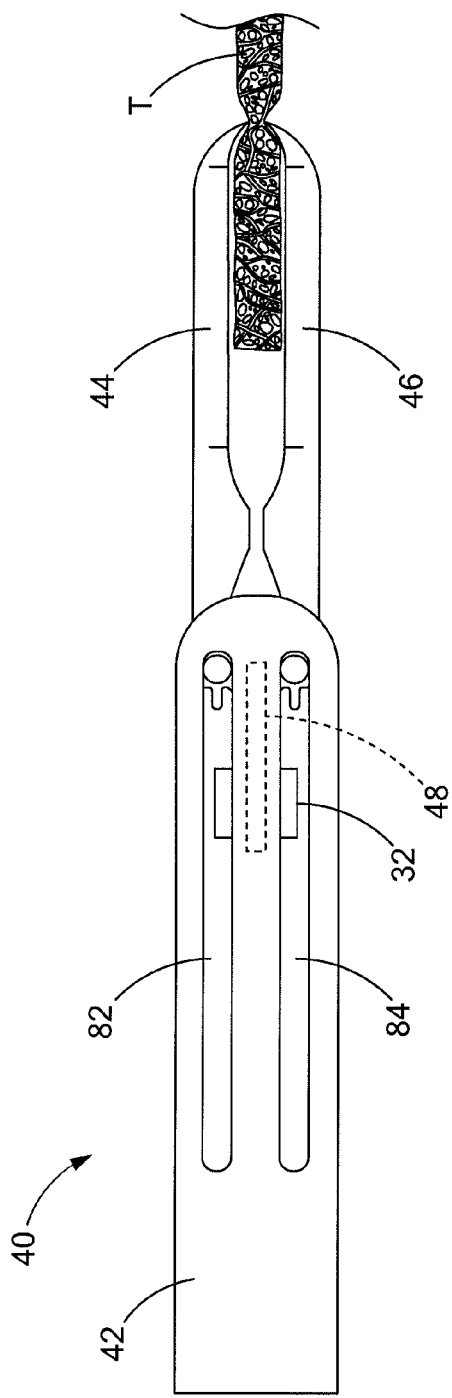
Figure 12:
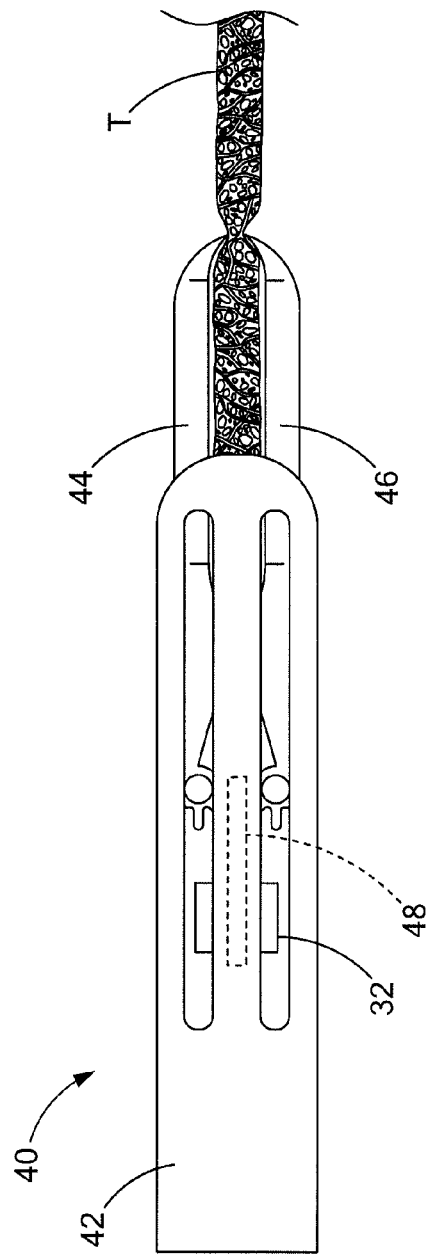

In the tissue receiving configuration shown in FIG. 10, the medical device 40 and its jaws 44, 46 may be positioned adjacent tissue T. As shown in FIG. 11, the tissue T may be placed between the first and second jaws 44, 46 and the jaws 44, 46 rotated back towards their position shown in FIG. 9. The tissue T has been shown as a single layer, although multiple layers may be clipped between the jaws 44, 46. Generally, proximal retraction of the drive wire 22 and the driver 48 again causes rotation of the first and second jaws 44, 46 to grasp the tissue T therebetween. As shown in FIG. 12, further proximal retraction of the drive wire 22 and driver 48 will cause the jaws 44, 46 to move longitudinally in a proximal direction (to the left on the page in FIG. 12).

Figure 13:
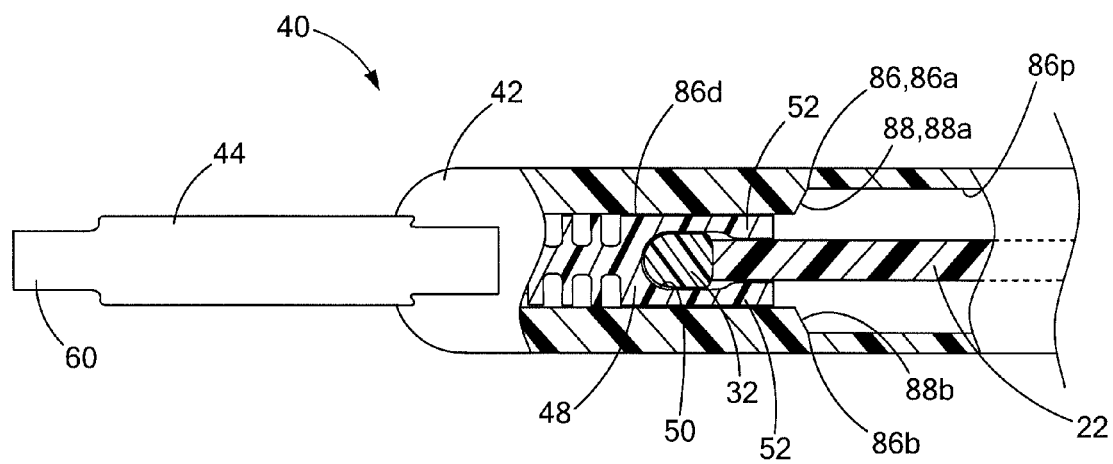
FIGS. 13 and 14 are top views, partially in cross-section, depicting operation of the medical system and device depicted in FIGS. 1-4.
Figure 14:
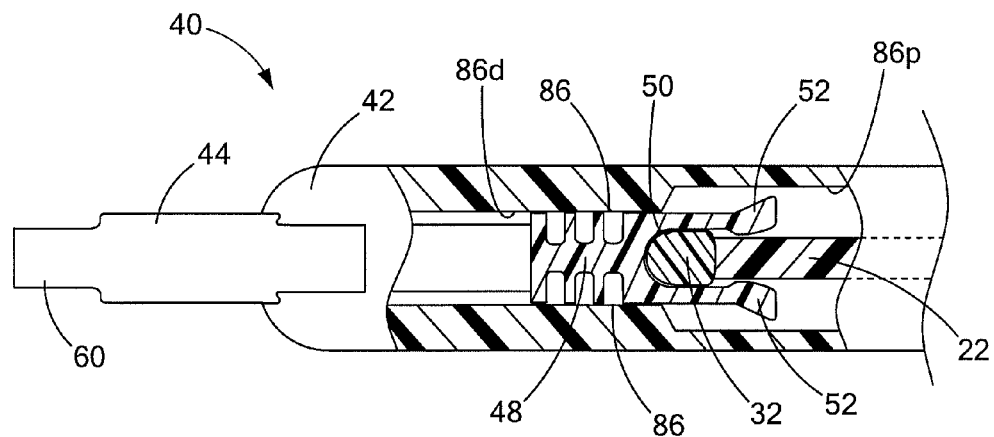

In order for the medical device 40 to serve as a clip and maintain its grasp on the tissue T, or to maintain the clipping of two layers of tissue against each other, the jaws 44, 46 may be locked in position and the drive wire 22 of the medical system 20 disconnected from the medical device 40. As shown in FIG. 13, the third guide surface 86 (which guides the driver 48) includes a proximal portion 86*p* and a distal portion 86*d*. The proximal portion 86*p* of the third guide surface 86 has a width (measured up and down on the page in FIG. 13) that is greater than a width of the distal portion 86*d* of the third guide 86. As previously discussed, the third guide surface 86 is formed by opposing surfaces or C-shaped channels 86*a*, 86*b* of the housing 42. The transition between the proximal portion 86*p* and distal portion 86*d* defines a shoulder 88, and namely two shoulders 88*a*, 88*b* on opposing sides of the housing 42. The shoulders 88*a*, 88*b* are sized and positioned to engage the opposing locking tabs 52 located on the driver 48.

As shown in FIG. 13, when the driver 48 is located within the distal portion 86*d* of the third guide surface 86, the locking tabs 52 are forced radially inwardly into firm frictional engagement with the drive wire 22. Stated another way, the socket 50 formed by the driver 48 to receive the distal head 32 has an entrance which is narrowed by the inward deflection of the locking tabs 52. In this state depicted in FIG. 13, the drive wire 22 is firmly engaged with the driver 48 and hence the first and second jaws 44, 46. When the drive wire 22 and driver 48 are retracted proximally, for example upon grasping tissue as shown in FIG. 12, the proximal end of the driver 48 is received within the proximal portion 86*p* of the third guide surface 86 which has a larger width that permits outward movement of the locking tabs 52. Accordingly, in the state depicted in FIG. 14, the locking tabs 52 may be loosely and detachably connected to the distal head 32 of the drive wire 22. That is, the proximal retraction of the jaws 44, 46 will be limited by either the tissue T engaging the distal end of the housing 42, or the pins 80 will abut the proximal ends of the slots 82*a*, 82*b*, 84*a*, 84*b* defining a first and second guide surfaces 82, 84. As such, when proximal movement of the jaws 44, 46 and the driver 48 are thus limited, further proximal movement of the drive wire 22 and its distal head 32 may be used to withdraw the distal head 32 from the socket 50 of the driver 48. This operation may also be used to further deflect the locking tabs 52 radially outwardly. In the event the natural elasticity of the tissue T tends to pull the jaws 44, 46 out from the housing towards their extended position, the locking tabs 52, 54 will abut the shoulders 88*a*, 88*b* of the third guide surface of the housing 42 to prevent further distal movement of the jaws 44, 46.

In one preferred embodiment the locking tabs 52 are plastically deformable, and may be bent around the distal head 32 of the drive wire 22 during manufacture. The driver 48 and its tabs 52 may thus have an initial size to slide within the distal portion 86*d* of the third guide surface 86, and proximal retraction of the drive wire 22 and distal head 32 of a predetermined force will plastically deform the locking tabs 52 outwardly into a position to engage the shoulders 88*a*, 88*b* and lock the clip by preventing distal movement of the jaws 44, 46 therebeyond.

Figure 15:
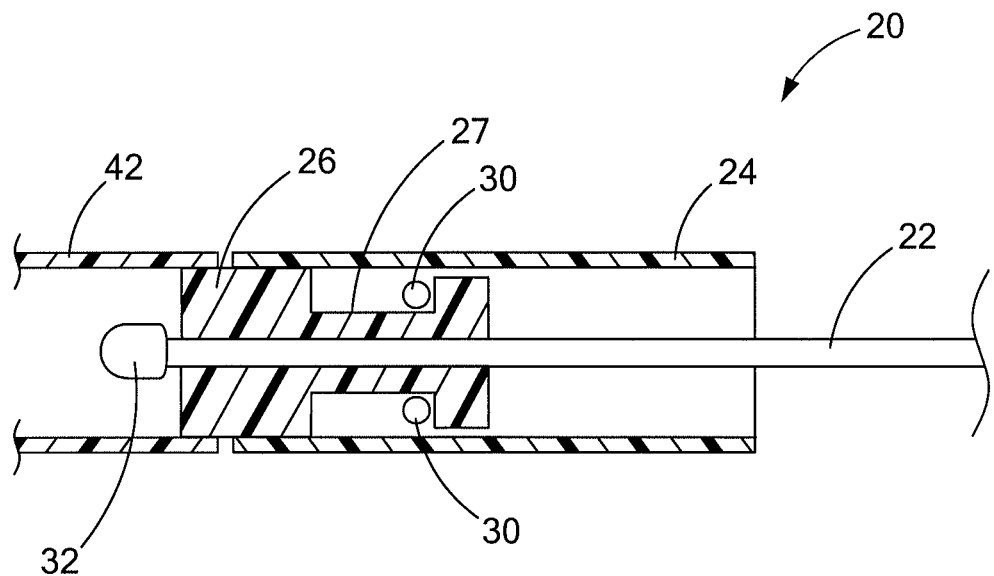
FIGS. 15 and 16 are cross-sectional views showing operation of the medical system depicted in FIGS. 1-4.
Figure 16:
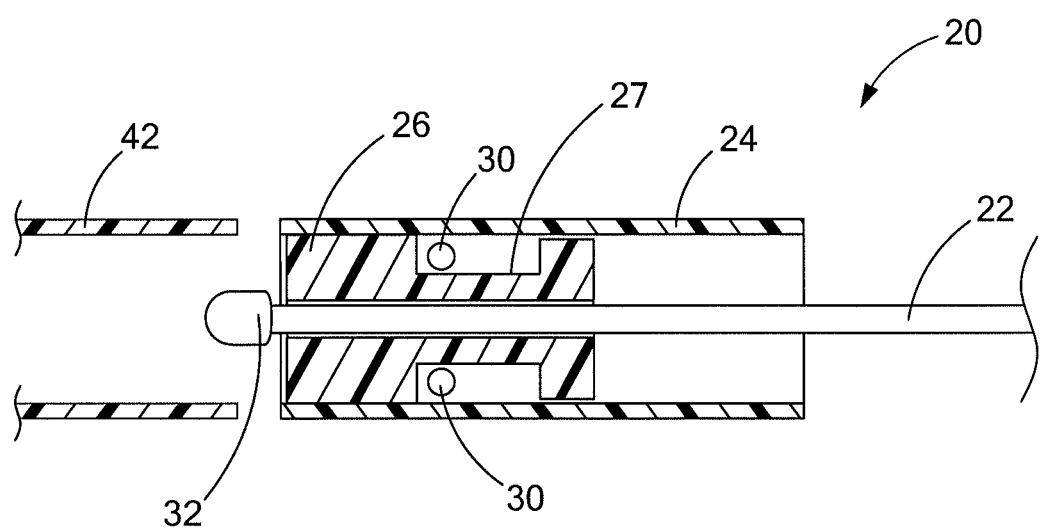
Figure 17:
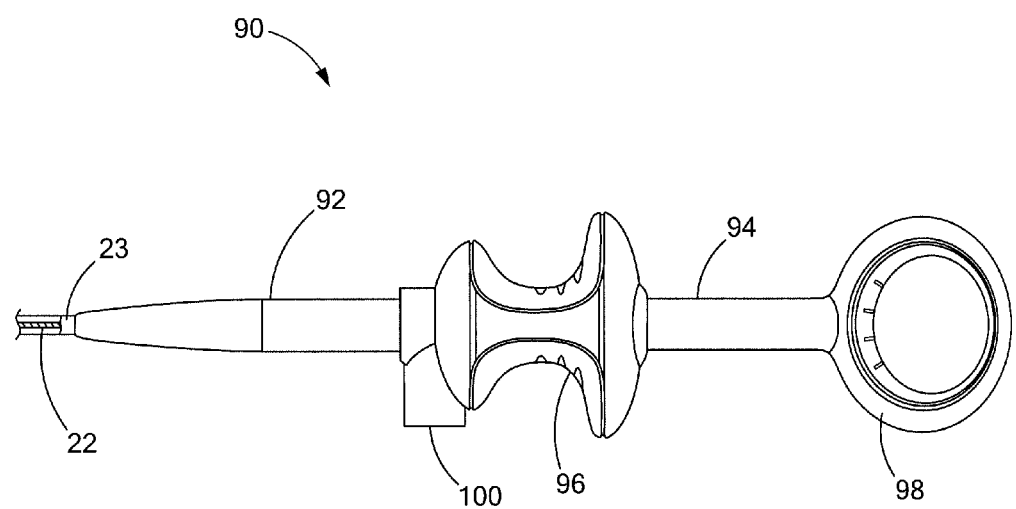
FIG. 17 is a side view of a handle forming a portion of the medical system of FIG. 1.

Turning now to FIGS. 15 and 16, upon still further proximal retraction of the drive wire 22 and distal head 32, the enlarged distal head 32 will abut the connection block 26 which is slidably fitted within the tubular connector 24. Sufficient proximal force on the drive wire 22 will overcome the frictional fit between the connection block 26 and the proximal end of the housing 42, thus moving the connection block 26 proximally (to the right on the page of FIGS. 15 and 16) to retract the connection block 26 within the tubular connector 24. An elongate sheath 23 slidably encases the drive wire 22, and extends proximally therealong to the proximal end of the device. The sheath 23 can be used to provide a counterforce on the connector 24 and housing 42 while proximally retracting the drive wire 22 and connection block 26. Accordingly, the drive wire 22, tubular connector 24 and connection block 26 may be fully disconnected from the medical device 40, thereby leaving the first and second jaws 44, 46 and the housing 42 in a state having the tissue T clipped between the jaws 44, 46 and retained in vivo.

It will be recognized by those skilled in the art that the drive wire 22 and its distal head 32 could again be connected to the driver 48 and its socket 50, thus permitting additional manipulation of the medical device to adjust the clipped tissue T. Likewise, additional medical devices may be attached to the drive wire 22 and tubular connector 24 of the medical system 20 for deployment of the additional medical devices, e.g. multiple devices 40 for clipping the tissue T may be used to close a perforation or achieve hemostasis. Generally, the support ring 34 (FIGS. 1-4) fixed on the drive wire 22 can be used to limit the distal movement of the drive wire 22, and can be distally advanced to a position abutting the connection block 26. As such, the drive wire 22 and support ring 34 can be used to push the connection block 26 distally out of the tubular connector 24 so that it can be attached to the housing (e.g. 42) of a new medical device (e.g. 40), or the previously placed medical device 40. Alternatively, the user may manually press (i.e. with fingers or a tool) the connection block 26 distally out of the tubular connector 24 for connection to another medical device.

The medical system 20 also includes a proximal end device for operating the medical device 40, and preferably a handle 90 as shown. The handle 90 includes an outer member 92 slidably receiving an inner member 94. The outer member 92 is a tubular member defining a passageway that receives the inner member 94, and includes a spool 96 formed on the outer surface which is shaped to be gripped by the fingers of the medical professional. The inner member 94 may be tubular or rod shaped, and includes a thumb ring 98 at its proximal end for gripping by the professional. The outer member 92 is attached to the sheath 23, which is preferably a coated coiled wire catheter as is known in the art. The inner member 94 is connected to the drive wire 22. In this way, translation of the inner member 94 and thumb ring 98 relative to the outer member 92 and spool 96 causes relative translation of the drive wire 22 relative to the sheath 23. This in turn operates the medical device 40, namely the clip defined by the housing 42 and jaws 44, 46 which rotate relative thereto, as previously described. A side port 100 may also be provided in communication with the interior passageway of the outer member 92 and sheath 23 for injection of fluids or other agents for facilitating hemostasis, closure, cleaning or other aspects related to the methods described above.

It will be recognized by those skilled in the art that, while the methods described above generally include placing the tissue devices in tissue through an internal bodily lumen, it will be recognized that the systems, devices and methods may be used on any layer of material (e.g. fabrics, cloth, polymers, elastomers, plastics and rubber) that may or may not be associated with a human or animal body and a bodily lumen. For example, the systems, devices and methods can find use in laboratory and industrial settings for clipping (or cutting, ligating, grasping) one or more layers of material that may or may not find application to the human or animal body, and likewise closing holes or perforations in layers of material that are not bodily tissue. Some examples include sewing or stitching and related manufacturing, working with synthetic tissues, connecting or repairing polymeric sheets, animal studies, veterinary applications, and post-mortem activities.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method for clamping tissue, the method comprising the steps of:
providing a medical system comprising a housing defining a longitudinal axis extending between proximal and distal ends of the housing, first and second jaws slidably and pivotally connected to the housing, a driver engaged with the first and second jaws for longitudinal movement and rotational movement of the first and second jaws, and an elongated drive wire selectively connected to the driver for longitudinal movement therewith;
advancing the drive wire distally to translate the first and second jaws distally relative to the housing;
restricting distal translation of the first and second jaws relative to the housing;
advancing the drive wire distally to rotate the first and second jaws away from each other;
positioning the tissue between the first and second jaws;
retracting the drive wire proximally to rotate the first and second jaws towards each other to clamp the tissue therebetween;
retracting the drive wire proximally to translate the first and second jaws proximally relative to the housing; and
detaching the drive wire from the driver to leave the first and second jaws clamped to the tissue and connected to the housing.

2. The method of claim 1, wherein the step of restricting distal translation of the first and second jaws relative to the housing occurs prior to the step of advancing the drive wire distally to rotate the first and second jaws.

3. The method of claim 2, wherein the housing includes a jaw guide surface guiding movement of the first and second jaws, the jaw guide surface including structure to restrict distal movement of the first and second jaws, and wherein the step of advancing the drive wire distally to rotate the first and second jaws occurs while the structure of the jaw guide surface is restricting distal movement of the first and second jaws.

4. The method of claim 2, wherein the step of restricting distal translation of the first and second jaws relative to the housing also occurs concurrently with the step of advancing the drive wire distally to rotate the first and second jaws.

5. The method of claim 1, wherein the drive wire is advanced distally to translate the first and second jaws distally relative to the housing, then the distal translation of the first and second jaws relative to the housing is restricted, and then the drive wire is advanced distally to rotate the first and second jaws.

6. The method of claim 1, wherein the housing restricts proximal translation of the first and second jaws while the drive wire is retracted proximally to rotate the first and second jaws towards each other.

7. The method of claim 1, further comprising the step of restricting the distal movement of the driver to maintain the clamping of the tissue between the first and second jaws.

8. The method of claim 7, wherein the housing includes a driver guide surface defining a shoulder, and where the driver includes a deflectable tab, and wherein the step of restricting the distal movement of the driver to maintain the clamping of the tissue occurs while the deflectable tab is engaged with the shoulder.

9. The method of claim 8, where the deflectable tab plastically deforms to a position engaged with the shoulder.

10. The method of claim 8, wherein the housing and driver are structured to permit the drive wire to disengage the driver when the deflectable tab is proximal to the shoulder.

11. The method of claim 7, wherein the steps of detaching and restricting occur simultaneously by sufficient proximal force on the drive wire to deflect a locking tab formed on the driver.

12. The method of claim 1, wherein the driver includes a deflectable tab, and wherein the housing includes a driver guide surface defining a shoulder positioned to engage the deflectable tab, and wherein sufficient distal force on the drive wire causes deflection of the deflectable tab such that the deflectable tab moves distally beyond the shoulder.

13. The method of claim 12, wherein the housing is structured to force the deflectable tab to frictional engage the drive wire when the deflectable tab is distal to the shoulder such that the drive wire and the driver move together.

14. The method of claim 1, wherein the step of detaching the wire guide includes placing a proximally directed force on the drive wire.

15. The method of claim 14, wherein the driver includes a socket defined by a locking tab, the socket receiving a distal end of the drive wire, and wherein sufficient proximally directed force causes plastic deformation of the locking tab.

16. The method of claim 1, further comprising a tubular connector slidably receiving the drive wire, the tubular connector slidably housing a connection block, the connection block sized and structured to frictionally engage both the tubular connector and the housing, and further comprising the step of proximally translating the drive wire such that it engages the connection block and proximally translates the connection block out of engagement with the housing.

17. The method of claim 16, wherein connection block includes a bore receiving the drive wire, and wherein the drive wire includes an enlarged distal end having a diameter greater than a diameter of the bore, whereby the enlarged distal end engages the connection block to proximally translate the connection block out of engagement with the housing.

18. A method for clamping tissue, the method comprising the steps of:
providing a medical system comprising a housing, first and second jaws, a driver and an elongated drive wire, the housing defining a longitudinal axis extending between proximal and distal ends of the housing, the first and second jaws slidably and pivotally connected to the housing, the driver engaged with the first and second jaws for driving longitudinal movement and rotational movement of the first and second jaws, the housing including a driver guide surface defining a shoulder, the driver including a deflectable tab, the elongated drive wire selectively connected to the driver for longitudinal movement therewith;

advancing the drive wire distally to translate the first and second jaws distally relative to the housing and to rotate the first and second jaws away from each other;

positioning the tissue between the first and second jaws;

retracting the drive wire proximally to rotate the first and second jaws towards each other and to translate the first and second jaws proximally relative to the housing, to clamp the tissue therebetween;

retracting the drive wire proximally to plastically deform the locking tab into a position for engagement with the shoulder such that distal movement of the driver is restricted to maintain the clamping of the tissue; and detaching the drive wire from the driver to leave the first and second jaws clamped to the tissue and connected to the housing.

19. The method of claim 18, wherein sufficient distal force on the drive wire causes deflection of the deflectable tab such that the deflectable tab moves distally beyond the shoulder, whereby the deflectable tab frictionally engages the drive wire such that the drive wire and the driver move together.

20. A method for clamping tissue, the method comprising the steps of:

providing a medical system comprising a housing, first and second jaws, a driver, a tubular connector, and an elongated drive wire, the housing defining a longitudinal axis extending between proximal and distal ends of the housing, the first and second jaws slidably and pivotally connected to the housing, the driver engaged with the first and second jaws for driving longitudinal movement and rotational movement of the first and second jaws, the tubular connector slidably housing a connection block, the connection block sized and structured to frictionally engage both the tubular connector and the housing, the elongated drive wire selectively connected to the driver for longitudinal movement therewith;

advancing the drive wire distally to translate the first and second jaws distally relative to the housing and to rotate the first and second jaws away from each other;

positioning the tissue between the first and second jaws;

retracting the drive wire proximally to rotate the first and second jaws towards each other and to translate the first and second jaws proximally relative to the housing, to clamp the tissue between the first and second jaws;

detaching the drive wire from the driver to leave the first and second jaws clamped to the tissue and connected to the housing; and retracting the drive wire proximally such that the drive wire engages the connection block and proximally translates the connection block out of engagement with the housing.

* * * * *